United States Patent [19]
Butts

[11] Patent Number: 6,127,446
[45] Date of Patent: Oct. 3, 2000

[54] IRRADIATION-CURABLE SILICONE COMPOSITIONS, PHOTO-ACTIVE PLATINUM (IV) COMPOUNDS, AND METHOD

[75] Inventor: Matthew David Butts, Rexford, N.Y.

[73] Assignee: General Electric Company, Schenectady, N.Y.

[21] Appl. No.: 09/303,407

[22] Filed: May 3, 1999

[51] Int. Cl.[7] .............................. G08G 77/50; C08J 3/28; C08F 4/80; C07F 17/02; C07F 7/08

[52] U.S. Cl. ............................ 522/66; 522/99; 522/29; 528/15; 528/31; 556/9; 556/11; 556/12; 556/136

[58] Field of Search ................... 556/9, 11, 12, 556/136; 522/29, 66, 99; 528/15, 31

[56] References Cited

U.S. PATENT DOCUMENTS

| | | |
|---|---|---|
| 4,510,094 | 4/1985 | Drahnak . |
| 4,600,484 | 7/1986 | Drahnak . |
| 4,916,169 | 4/1990 | Boardman et al. . |
| 5,659,054 | 8/1997 | Wilson . |
| 5,776,997 | 7/1998 | Hafner et al. . |

OTHER PUBLICATIONS

"Reactions of (π–1,5–cyclooctadiene)organoplatinum(II) Compounds and the Synthesis of Perfluoroalkylpatinum Complexes", by H.C. Clark et al., Journal of Organometallic Chemistry, 59 (1973) 411–428.

"195Pt NMR Study of (η5–Cyclopentadienyl)trialkylplantinum(IV) Complexes", by L.D. Boardman et al., Magnetic Resonance in Chemistry, voo. 30, 481–489 (1992).

"(η5–Cyclopentadienyl)trialkylplatinum Photohydrosilylation Catalysts. Mechanism of Active Catalyst Formation and Preparation of a Novel Bis(silyl)platinum Hydride", by L.D. Boardman, Organometallics 1992,11, 4194–4201.

*Primary Examiner*—Susan W. Berman
*Attorney, Agent, or Firm*—Noreen C. Johnson; Douglas E. Stoner

[57] ABSTRACT

Cyclopentadienylplatinum (IV) compounds having a trisubstituted-silyl aliphatic group attached to platinum by carbon-platinum linkages have been found to be photoactive and effective as hydrosilylation catalysts in irradiation-curable silicone mixtures.

34 Claims, No Drawings

IRRADIATION-CURABLE SILICONE COMPOSITIONS, PHOTO-ACTIVE PLATINUM (IV) COMPOUNDS, AND METHOD

BACKGROUND OF THE INVENTION

The present invention is directed to photo-active cyclopentadienylplatinum (IV) compounds, and to irradiation-curable silicone compositions containing such compounds as photo-active platinum (IV) catalysts.

Drahnak, U.S. Pat. No. 4,600,484, is directed to a hydrosilylation process involving the addition between silicon-bonded hydrogen compounds and compounds containing aliphatic unsaturation. Drahnak teaches that his process is activated by actinic radiation. Drahnak uses a platinum complex, for example, $CpPt(R)_3$, as a catalyst, where R is a $C_{1-8}$ aliphatic organic radical. The Drahnak catalyst has a cyclopentadienyl group, Cp, eta-bonded to a platinum (IV) atom which is substituted with three sigma-bonded aliphatic radicals, and is shown as $—Pt(CH_3)_3$. It is also reported in U.S. Pat. No. 4,600,484, that the cyclopentadienyl group, Cp, in the $CpPt(R)_3$ catalyst can be further modified with organosilyl groups.

In Clark, H. C. and Manzer, L. E., J. Organomet. Chem, 1973, 59, 411, it is reported that $(COD)Pt[CH_2Si(CH_3)_3]_2$ can be synthesized using a 1,4-cyclooctadienyl ligand, referred to as COD. However, efforts to eliminate the COD group and substitute it with an alkyl radical to produce a mixed alkyl, organosilicon species, such as a Pt(IV) compound capable of reacting with a Cp(M) compound to form an effective photo-active compound were unsuccessful. More recently, Boardman, L. D. and Newmark, R. A. Mag. Res. Chem. 1992, 30, 481 disclosed that CpPt(IV) complexes having bulky organic groups can be joined to platinum.

It would be desirable therefore to provide additional useful photo-active platinum (IV) compounds to effect the cure of irradiation-curable silicone compositions involving addition between silicon-bonded hydrogen compounds and materials containing aliphatic unsaturation.

Further, it also would be desirable to provide photo-active platinum compounds comprising a cyclopentadienyl group chemically combined to a Pt(IV) group, where the cyclopentadienyl group can be free of organic radicals, or substituted with up to five organic radicals, such as a $C_{1-22}$ organic radical, which can include an aromatic radical, such as a phenanthryl radical, or an aliphatic radical, or a mixture thereof; and the Pt(IV) group can have attached to platinum by a carbon-Pt linkage, at least one organosilicon radical, for example, $CH_2Si(CH_3)_3$, and also include one or more aliphatic or aromatic radicals attached to platinum.

BRIEF SUMMARY OF THE INVENTION

In one of its embodiments the present invention comprises photo-active cyclopentadienylplatinum (IV) compounds having a trisubstituted-silyl aliphatic group attached to platinum by a carbon-platinum bond.

In another of its embodiments the present invention comprises photo-active cyclopentadienylplatinum (IV) compounds having the formula, $$[(R^1)_a(R^2)_bCP]Pt(R^3R^4)Q, \quad (1)$$

where $R^1$ is a $C_{6-20}$ aromatic radical, $R^2$, $R^3$, and $R^4$ are each independently a $C_{1-22}$ aliphatic organic radical, Cp is a cyclopentadienyl radical, Q is a silicon-containing organic sensitizing group, "a" and "b" are whole numbers independently equal to 0 to 5 inclusive, and the sum of "a+b" is equal to 0 to 5 inclusive.

In another of its embodiments the present invention comprises a method for making platinum (IV) compounds included within the formula $[(R^1)_a(R^2)_bCp]Pt(R^3R^4)Q$, where $R^1$, $R^2$, $R^3$, $R^4$, Cp, Q, "a", and "b" are as previously defined, comprising, effecting reaction between a cyclopentadienide compound of the formula $(R^1)_a(R^2)_bCpM$, and a platinum (IV) compound of the formula, $XPt(R^3R^4)Q$, where M is a metallic anion, and X is an anionic leaving group.

In still another of its embodiments the present invention comprises platinum (IV) compounds having the formula, $$XPt(R^3R^4)Q, \quad (3),$$

where Q is a silicon-containing group having the formula, $—R^5Si(R^6)_3$, X is an anionic leaving group, $R^3$ and $R^4$ are each independently a $C_{1-22}$ aliphatic organic radical, $R^6$ is a $C_{1-12}$ organic radical, and $R^5$ is a $C_{1-4}$ alkylene or alkylidene radical.

In another of its embodiments the present invention comprises a method for making platinum (IV) compounds included within the formula $XPt(R^3R^4)Q$, which comprises, (a) effecting reaction between a platinum (II) compound $ZPt(R^3)X$ and an organosilicon compound MQ, to form platinum (II) compound having the formula, $ZPt(R^3)Q$, and (b) effecting reaction between the platinum (II) compound of (a) and a haloaliphatic compound $XR^4$, where Z is a $C_{7-10}$ cyclodienyl group, and $R^3$, $R^4$, Q, M and X are as previously defined.

In still another of its embodiments the present invention comprises an irradiation-curable silicone composition comprising, (a) a polydiorganosiloxane having at least two alkenyl radicals attached to silicon by carbon-silicon bonds, where the alkenyl radicals can be in the terminal position, or in the polymer backbone, or a combination thereof, (b) a silicon hydride cross-linker, and, (c) an amount of a photo-active cyclopentadienylplatinum (IV) compound having a trisubstituted-silyl aliphatic group attached to platinum by carbon-platinum bonds which is sufficient to effect the cure of the irradiation-curable silicone composition.

In still another of its embodiments the present invention comprises a method of coating a substrate with a cured tack-free silicone film, which comprises, (1) applying onto the surface of the substrate to a thickness of about 0.5 to about 5 mil, an irradiation-curable silicone composition comprising, (a) a polydiorganosiloxane having at least two alkenyl radicals attached to silicon by carbon-silicon bonds, where the alkenyl radicals can be in the terminal position, or in the polymer backbone, or a combination thereof, (b) a silicon hydride cross-linker, and, (c) an amount of a photo-active cyclopentadienylplatinum (IV) compound having a trisubstituted-silyl aliphatic group attached to platinum by carbon-platinum bonds which is sufficient to effect the cure of the irradiation-curable silicone composition, and (2) irradiating the surface of the applied irradiation-curable silicone composition with light in the range of 240–400 nm.

In still other of its embodiments the present invention comprises substrates coated with an irradiation-curable silicone composition and the corresponding substrates coated with the subsequently cured silicone film comprising platinum (IV) compounds included within formula (1), and any reaction products thereof which may have been formed, for example, during processing and irradiation-curing.

DETAILED DESCRIPTION OF THE INVENTION

The present invention is based on the discovery that cyclopentadienylplatinum (IV) compounds having a silicon-containing organic sensitizing group bound to platinum by a Pt-C bond, as shown in formula (1)

$$[(R^1)_a(R^2)_bCP]Pt(R^3R^4)Q, \quad (1)$$

are highly efficient catalysts for irradiation-curable compositions.

Photo-active cyclopentadienylplatinum (IV) compounds of formula (1) can be synthesized by effecting reaction between a cyclopentadienyl species having the formula, $$(R^1)_a(R^2)_bCpM, \quad (2)$$

and a platinum (IV) compound having the formula, $$XPt(R^3R^4)Q, \quad (3),$$

where $R^1$ is a $C_{6-20}$ aromatic organic radical, $R^2$ is a $C_{1-22}$ aliphatic organic radical, $R^3$ and $R^4$ are each independently a $C_{1-22}$ aliphatic organic radical or a $C_{6-20}$ aromatic organic radical, Cp is a cyclopentadienyl radical, M is a metallic anion, such as lithium, X is an anionic leaving group, such as, but not limited to, triflate, borate, phosphate, or halogen, Q is a trisubstituted-silyl aliphatic group of the formula —$R^5Si(R^6)_3$, $R^6$ is a $C_{1-12}$ organic radical, and $R^5$ is a $C_{1-4}$ alkylene or alkylidene radical, "a" and "b" are whole numbers independently equal to 0 to 5 inclusive, and the sum of "a+b" is equal to 0 to 5 inclusive.

Platinum (IV) compounds included within formula (3) can be made in a stepwise manner from a Pt (II) compound having the formula, $$ZPt(R^3)X \quad (4)$$

and a silicon sensitizing group, MQ, to form a silicon-containing Pt (II) compound containing a silicon sensitizing group as shown by the following equation:

$$ZPt(R^3)X + MQ \rightarrow ZPt(R^3)Q \quad (5)$$

where $R^3$, X, Q, and M are as previously defined, and Z is a $C_{7-10}$ cyclodienyl group. Cyclodienyl groups within the context of the present invention include both simple cyclodienyl groups and bridged cyclodienyl groups, such as, but not limited to, cyclooctadienyl and norbornadienyl.

The product of formula (5) can be converted to a platinum (IV) compound included within formula (3) when reacted with a compound $XR^4$, where X is an anionic leaving group, such as, but not limited to, triflate, borate, phosphate, or halogen, and $R^4$ is as previously defined:

$$ZPt(R^3)Q + XR^4 \rightarrow XPt(R^3R^4)Q.$$

Although a variety of $XR^4$ compounds and reaction conditions can be employed in effecting the displacement of the Z group in $ZPt(R^3)Q$, a $C_{1-3}$ neat alkyl iodide is preferably employed, such as methyl iodide at a temperature of about 50° C. to about 100° C. from about 10 to about 48 hours.

Among the photo-active cyclopentadienylplatinum (IV) compounds of formula (1), there are included, (cyclopentadienyl)dimethyltrimethylsilylmethyl platinum; (cyclopentadienyl)diethyltrimethylsilylmethyl platinum; (cyclopentadienyl)dipropyltrimethylsilylmethyl platinum; (cyclopentadienyl)diisopropyltrimethylsilylmethyl platinum; (cyclopentadienyl)diallyltrimethylsilylmethyl platinum; (cyclopentadienyl)dibenzyltrimethylsilylmethyl platinum; (cyclopentadienyl)dimethyltriethylsilylmethyl platinum; (cyclopentadienyl)dimethyltripropylsilylmethyl platinum; (cyclopentadienyl) dimethyltriisopropylsilylmethyl platinum; (cyclopentadienyl)dimethyltriphenylsilylmethyl platinum; (cyclopentadienyl)dimethyldimethylphenylsilylmethyl platinum; (cyclopentadienyl) dimethylmethyldiphenylsilylmethyl platinum; (cyclopentadienyl)dimethyldimethyl(trimethylsiloxy) silylmethyl platinum; (cyclopentadienyl)dimethyldimethyl (dimethylvinylsiloxy)silylmethyl platinum; [(1'-naphthyl) cyclopentadienyl]trimethylsilylmethylplatinum; [(2'-naphthyl)cyclopentadienyl]trimethylsilylmethylplatinum; [1-methyl-3-(1'-naphthyl)cyclopentadienyl] trimethylsilylmethylplatinum; [1-methyl-3-(2'-naphthyl) cyclopentadienyl]trimethylsilylmethylplatinum; [(4'-biphenyl)cyclopentadienyl]trimethylsilylmethylplatinum; [1(4'-biphenyl)-3-methylcyclopentadienyl] trimethylsilylmethylplatinum; [(9'-phenanthryl) cyclopentadienyl]trimethylsilylmethylplatinum; [1-methyl-3-(9'-phenanthryl)cyclopentadienyl] trimethylsilylmethylplatinum; [1-(2'-anthracenyl)-3-methylcyclopentadienyl]trimethylsilylmethylplatinum; [(2'-anthracenyl)cyclopentadienyl] trimethylsilylmethylplatinum; [(1'-pyrenyl) cyclopentadienyl]trimethylsilylmethylplatinum; [1-methyl-3-(1'-pyrenyl)cyclopentadienyl] trimethylsilylmethylplatinum.

The cyclopentadienyl ring shown in the above compounds can be replaced with a cyclopentadienyl ring substituted with one or more radicals selected from methyl, chloro, fluoro, trimethylsilyl, triethylsilyl, dimethylphenylsilyl, methyldiphenylsilyl, triphenylsilyl, phenyl, fluorophenyl, chlorophenyl, methoxy, naphthyl, biphenyl, anthracenyl, pyrenyl, 2-benzoylnaphthalene, thioxanthone, 2 chlorothioxanthone, 2-isopropylthioxanthone, anthraquinone, 1-chloroanthraquinone, acetophenone, benzophenone, 9,10-dimethylanthracene, 9,10-dichloroanthracene, and mixtures thereof. Further, the cyclopentadienyl ring can be substituted with an $\eta^5$-fluorenyl group.

Preferably the cyclopentadienyl group is unsubstituted or substituted with at least one aromatic organic radical, or substituted with at least one aliphatic organic radical, or with a mixture of at least one aromatic organic radical and at least one aliphatic organic radical. Preferred aromatic organic radicals are naphthyl, biphenyl, anthracenyl, phenanthryl and pyrenyl.

Aliphatic organic radicals included within $R^2$, $R^3$, and $R^4$ groups are $C_{1-22}$ aliphatic moieties which can independently be the same or different, and include methyl, ethyl, propyl, isopropyl, butyl, allyl, aryl-substituted aliphatic moieties such as, but not limited to, benzyl and substituted benzyl, and cycloaliphatic groups such as, but not limited to, cyclopentyl and cyclohexyl. Aromatic organic radicals included within $R^3$ and $R^4$ are $C_{6-20}$ aromatic moieties which can be the same or different, and include, but are not limited to, phenyl, and substituted phenyl, particularly alkyl-substituted phenyl. Mixtures of $C_{1-22}$ aliphatic moieties and $C_{6-20}$ aromatic moieties for $R^3$ and $R^4$ are also within the scope of the invention.

In preferred embodiments $R^2$, $R^3$, and $R^4$ groups are independently $C_{1-22}$ aliphatic moieties, more preferably independently $C_{1-12}$ aliphatic moieties, and most preferably independently C1-6 aliphatic moieties. In especially preferred embodiments of the present invention $R^2$, $R^3$, and $R^4$ groups are methyl.

The irradiation-curable silicone compositions of the present invention can be made by incorporating an effective amount of a photo-active platinum (IV) compound included within formula (1) into an irradiation-curable silicone blend comprising a polydiorganosiloxane, having at least two alkenyl radicals attached to silicon by carbon-silicon bonds, and a silicon hydride cross-linker. An effective amount of the photo-active platinum (IV) compound is an amount sufficient to provide from about 5 ppm to about 500 ppm of platinum, and preferably, about 10 to about 200 ppm based on the weight of irradiation-curable silicone mixture.

If any of the components of the irradiation-curable silicone composition is a solid or is extremely viscous, a solvent can be introduced into the composition to facilitate uniform mixing of the composition components. Suitable solvents include aromatic hydrocarbons, such as, but not limited to, xylene and toluene, aliphatic hydrocarbons, such as, but not limited to, hexane and mineral spirits, halogenated hydrocarbons, such as, but not limited to, dichloromethane, chlorobenzene and trichlorobenzene, and ethers, such as, but not limited to, tetrahydrofuran, methyltetrahydrofuran, and dioxane. From about 0.1 to about 10 parts of solvent per part by weight of the irradiation-curable silicone composition may be used. The resulting composition will generally be sufficiently pure for its intended use. However, it may be desirable to remove the solvent, if one has been employed, by any convenient means known in the art.

As used hereinafter, the expression "irradiation-curable" refers to the ability to convert an irradiation-curable silicone composition to a non-smear, tack-free film, after it has been applied in a continuous, semi-continuous, or batch manner onto a substrate, such as a paper substrate, a plastic substrate, or a metal substrate, to a thickness of about 0.5 to about 5 mils. Suitable lamps, which can be used to effect an irradiation cure, can operate in the range of about 240 nanometers (nm) to about 400 nm, and preferably, about 240 nm to about 350 nm. Depending on lamp intensity, which can vary over about 200 watts (W) to about 600 W, a continuous application rate can vary over a line speed of about 50 feet per minute (ft/min) to about 1500 ft/min.

While a variety of irradiation-curable coating compositions are included within the scope of the present invention, a preferred variety of coating compositions are useful in the paper coating art. Accordingly, the alkenyl-containing polydiorganosiloxane, which preferably consists essentially of chemically combined dimethylsiloxy units, can be a polydimethylsiloxane having vinyl radicals attached to silicon. While vinyl radicals can be in the backbone or in the terminal position, vinyl terminated polydimethylsiloxane is particularly preferred. The vinylsiloxy unit content can be about 0.05 to about 3.5 mole percent, and preferably, about 0.14 to about 1.7 mole percent based on total siloxy units.

While dimethylsiloxy units are preferred, other diorganosiloxy units which can be in the backbone include for example, methylphenylsiloxy units, methyltrifluoropropylsiloxy units, and diphenylsiloxy units.

The alkenyl-containing polydiorganosiloxane can have a viscosity of about 100 centipoise to about 10,000 centipoise at 25° C., and preferably about 150 centipoise to about 600 centipoise. The silicon hydride cross-linker can be present in the irradiation-curable coating composition at from about 0.1 part to about 10 parts by weight, based on 100 parts by weight of the alkenyl-containing polydiorganosiloxane. The silicon hydride cross-linker can have a viscosity of about 20 to about 1000 centipoise, and preferably about 30 to about 40 centipoise, and can have about 0.04% to about 1.4% by weight of hydrogen attached to silicon.

In still another of its embodiments the present invention comprises a method of coating a substrate with a cured tack-free silicone film, which comprises,
  (1) applying onto the surface of the substrate to a thickness of about 0.5 to about 5 mil, an irradiation-curable silicone composition comprising,
    (a) a polydiorganosiloxane having at least two alkenyl radicals attached to silicon by carbon-silicon bonds, where the alkenyl radicals can be in the terminal position, or in the polymer backbone, or a combination thereof,
    (b) a silicon hydride cross-linker, and,
    (c) an amount of a photo-active cyclopentadienylplatinum (IV) compound having a trisubstituted-silyl aliphatic group attached to platinum by carbon-platinum bonds which is sufficient to effect the cure of the irradiation-curable silicone composition, and
  (2) irradiating the surface of the applied irradiation-curable silicone composition with light in the range of 240–400 nm.

Still other embodiments of the present invention comprise substrates coated with an irradiation-curable silicone composition and the corresponding substrates coated with the subsequently cured silicone film comprising platinum (IV) compounds included within formula (1), and any reaction products thereof which may have been formed, for example, during processing and irradiation-curing. Suitable substrates which can be coated with a curable silicone composition and subsequently cured silicone film include, but are not limited to, cellulose-based substrates, such as paper, preferably Glassine or super-calendered Kraft paper, and film substrates, such as polyethylene, polypropylene, and polyester, such as Mylar, and hybrid substrates, such as those comprising polyethylene-Kraft paper or polypropylene-Kraft paper. Suitable substrates also include those which are substantially non-porous, such as glass or metal.

In order that those skilled in the art will be better able to practice the invention, the following examples are given by way of illustration and not by way of limitation. All parts are by weight unless otherwise indicated.

EXAMPLE 1

The synthesis of $IPt(CH_3)_2CH_2Si(CH_3)_3$ was based on the employment of $(1,4\text{-cyclooctadienyl})Pt(CH_3)Cl$ as a starting material. The latter was prepared in accordance with the procedure shown by Clark, H. C. and Manzer, L. E., J. Organomet. Chem, 1973, 59, 411, which is incorporated herein by reference.

There was added under argon, 10 milliliters (mL) of anhydrous tetrahydrofuran to a flame dried flask containing 398.9 milligrams (mg) (1.128 millimoles [mmol]) of $(1,4\text{-cyclooctadienyl})Pt(CH_3)Cl$. A colorless solution was obtained which was cooled to 0° C.

There was added dropwise to the solution with stirring, 1.70 mL of a 0.67 M solution in pentane of trimethylsilylmethyllithium. The resulting solution turned yellow. The mixture was allowed to stir at 0° C. for an additional 45 minutes.

The solvent was removed under vacuum to form a dark viscous oil. There was added 25 mL of hexane to effect the precipitation of a tan product which was separated by centrifugation. After a second hexane wash, the combined hexane solutions were washed with distilled water to form a dark yellow organic layer. The washed product was dried over magnesium sulfate and centrifuged. The solvent was removed under vacuum to yield 417.0 mg (1.071 mmol, or a 95% yield) of (1,4-cyclooctadienyl)Pt($CH_3$)$CH_2Si(CH_3)_3$ as a viscous oil. The oil can be recrystallized from hexane at low temperature.

The (1,4-cyclooctadienyl)Pt($CH_3$)$CH_2Si(CH_3)_3$ was dissolved in 5 mL of neat iodomethane, and the solution was transferred to a Teflon® resin plug-sealed vessel. The flask was evacuated and flushed three times with argon and heated in the dark for two days at 60° C. The product was stripped under vacuum. There was obtained an 89% yield of a viscous oil. Based on method of preparation and NMR spectra, the product was the platinum compound IPt($CH_3$)$_2CH_2Si(CH_3)_3$. The compound can be recrystallized from hexane at low temperature.

The platinum compound was evaluated as a hydrosilylation catalyst. There was employed a sufficient amount of the platinum compound to provide 100 ppm of platinum, based on the weight of silicone mixture. The silicone mixture consisted of 95.2 parts of a vinyl-terminated polydimethylsiloxane having a viscosity of 200 centipoise at 25° C., and 4.8 parts of a trimethylsiloxy-terminated polysiloxane consisting essentially of a mixture of methylhydrogensiloxy units and dimethylsiloxy units. It was found that a complete cure of the silicone mixture was obtained after eight minutes at 115° C.

EXAMPLE 2

A series of $R^1(CH_3)_cCpPt(CH_3)_2Q$ compounds were prepared by effecting reaction between IPt($CH_3$)$_2CH_2Si(CH_3)_3$ and a cyclopentadienide compound selected from a variety of $R^1(CH_3)_cCpM$ compounds, where $R^1$, Cp, and Q are as previously defined, and c is a whole number equal to 0 or 1.

The respective $R^1(CH_3)_cCpPt(CH_3)_2Q$ compounds were then individually evaluated under both ambient light and darkness conditions as catalysts in an irradiation-curable silicone mixture. Evaluation was made by Photo-Differential Scanning Calorimetry using a Perkin-Elmer Photo-DSC system (DSC7+DPA7) employing a PEM500® multipower supply.

There was slowly added dropwise under argon at 0° C., a 7 mL tetrahydrofuran solution of 240 mg of lithium 1-methyl-3-(9'-phenanthryl)cyclopentadienide into a stirring solution of 401 mg of IPt($CH_3$)$_2(CH_2Si(CH_3)_3$ in 5 mL of tetrahydrofuran. At the end of the addition, there was formed a solution having a deep orange color.

The solution was stirred at 0° C. for 30 minutes and then allowed to warm to room temperature. After one hour, the solution was vacuum-stripped to form a viscous orange oil. The oil was thrice extracted with hexane and the extracts filtered through Celite®. The hexane solution of crude product was then washed three times with distilled water and dried over magnesium sulfate. The hexane solution was vacuum stripped to provide 405 mg (78% yield) of a tacky orange solid. Based on method of preparation, NMR spectroscopy, and mass spectrometry, the solid was $C_{14}H_9$($CH_3$)CpPt[$CH_3$]$_2CH_2Si(CH_3)_3$, or [1-methyl-3-(9'-phenanthryl)cyclopentadienyl]dimethyltrimethylsilylmethylplatinum (IV).

EXAMPLE 3

Additional $R^1(CH_3)_cCpPt(CH_3)_2Q$ compounds were prepared following the same procedure as Example 2, where $R^1$, Cp, Q, and "c" are as previously defined.

A platinum-catalyzed irradiation-curable silicone mixture also was prepared using commercially available $CH_3CpPt(CH_3)_3$.

The respective platinum compounds were weighed and respectively mixed vigorously with about 20 drops of toluene and introduced as a solution into a silicone mixture. There was employed sufficient platinum compound to provide 100 ppm of platinum, based on the weight of silicone mixture. The silicone mixture consisted of 95.2 parts of a vinyl-terminated polydimethylsiloxane having a viscosity of 200 centipoise at 25° C., and 4.8 parts of a trimethylsiloxy-terminated polysiloxane consisting essentially of a mixture of methylhydrogensiloxy units and dimethylsiloxy units and having a viscosity of 35 centipoise at 25° C.

In the following table, "Bath Life" was measured in the absence of light. Bath life is the time required for a curable silicone formulation to show a viscosity increase sufficient to interfere with free flow when shaken. As shown in the following table, $C_{10}H_7$ is a naphthyl group, and $C_{14}H_9$ is a phenanthryl group:

| Catalyst* | Bath Life |
|---|---|
| $CH_3CpPt(CH_3)_3$** | 24–48 hours |
| $C_{10}H_7(CH_3)CpPt(CH_3)_3$ | 96 hours |
| $C_{10}H_7(CH_3)CpPt[CH_3]_2CH_2Si(CH_3)_3$ | 96 hours |
| $C_{14}H_9(CH_3)CpPt(CH_3)_3$ | 120 hours |
| $C_{14}H_9(CH_3)CpPt[CH_3]_2CH_2Si(CH_3)_3$ | 96 hours |

*formulas refer to the compounds named in the above examples
**used as received from Strem Chemical, Inc., Newburyport, MA.

The "Bath Life" values show that the compositions of the present invention have suitable shelf-life stability in the absence of light.

EXAMPLE 4

Additional curable silicone formulations were prepared following the above procedure, and were used to treat Kraft paper in the absence of light using a Meyer bar rod. The respective treated papers were then exposed to the same fluorescent light source. The time required to form a tack-free surface was measured. The following results were obtained:

| Catalyst* | Tack-Free |
|---|---|
| $CH_3CpPt(CH_3)_3$ | >24 hours |
| $CpPt(CH_3)_2CH_2Si(CH_3)_3$ | 1 hour |
| $C_{10}H_7CH_3CpPt(CH_3)_2CH_2Si(CH_3)_3$ | 26 minutes |

*formulas refer to compounds named in the above examples

EXAMPLE 5

In accordance with the procedures of Example 3, other curable silicone formulations were prepared in the absence of light. Samples consisting of 2–3 mg formulations were added to aluminum pans. The cure profiles of the respective mixtures were measured using a Perkin-Elmer Photo-DSC system (DSC7+DPA7) with a PEM 500 multipower supply. The light source was a 200 watt Hg/Xe lamp. A temperature of 30° C. was maintained during the test procedure. The following results were obtained:

Photo-DSC Experiments

| Catalyst* | ΔH (J/g) | peak time (min) |
|---|---|---|
| $CH_3CpPt(CH_3)_3$ | −16.7 | 0.39 |
| $CpPt(CH_3)_2CH_2Si(CH_3)_3$ | −32.2 | 0.33 |
| $C_{10}H_7(CH_3)CpPt(CH_3)_3$ | −34.0 | 0.16 |
| $C_{10}H_7(CH_3)CpPt[CH_3]_2CH_2Si(CH_3)$ | −37.8 | 0.19 |
| $C_{14}H_9(CH_3)CpPt(CH_3)_3$ | −39.2 | 0.19 |
| $C_{14}H_9(CH_3)CpPt[CH_3]_2CH_2Si(CH_3)$ | −36.6 | 0.16 |

*formulas refer to compounds named above

The above results show that the silicon-containing platinum catalysts of the present invention can be used to provide improved irradiation-curable silicone coating compositions.

Although the above examples are directed to only a few of the very many variables which can be used in the practice of the present invention, it should be understood that the present invention is directed to the use of a much broader variety of cyclopentadienyl platinum (IV) compounds and the use of such compounds as catalysts in a wide variety of irradiation-curable silicon mixtures as set forth in the description preceding these examples.

What is claimed is:

1. A photo-active cyclopentadienylplatinum (IV) compound having a trisubstituted-silyl aliphatic group attached to platinum by a carbon-platinum bond.

2. A photo-active cyclopentadienylplatinum (IV) compound in accordance with claim 1, where the cyclopentadienyl is substituted with at least one aromatic organic radical.

3. A photo-active cyclopentadienylplatinum (IV) compound in accordance with claim 1, where the cyclopentadienyl is substituted with at least one aliphatic organic radical.

4. A photo-active cyclopentadienylplatinum (IV) compound in accordance with claim 1, where the cyclopentadienyl is substituted with a mixture of at least one aromatic organic radical and at least one aliphatic organic radical.

5. Photo-active cyclopentadienylplatinum (IV) compounds having the formula, $$[(R^1)_a(R^2)_bCp]Pt(R^3R^4)Q$$

where $R^1$ is a $C_{6-20}$ aromatic radical, $R^2$, $R^3$, and $R^4$ are each independently a $C_{1-22}$ aliphatic organic radical, Cp is a cyclopentadienyl radical, Q is a silicon-containing organic sensitizing group, "a" and "b" are whole numbers independently equal to 0 to 5 inclusive, and the sum of "a+b" is equal to 0 to 5 inclusive.

6. A photo-active cyclopentadienylplatinum (IV) compound in accordance with claim 5, where Q is $-R^5Si(R^6)_3$, $R^6$ is a $C_{1-12}$ organic radical, and $R^5$ is a $C_{1-4}$ alkylene or alkylidene radical.

7. A photo-active cyclopentadienylplatinum (IV) compound in accordance with claim 5, where $R^1$ is phenanthryl.

8. A photo-active cyclopentadienylplatinum (IV) compound in accordance with claim 5, where $R^1$ is naphthyl.

9. The compound (cyclopentadienyl)dimethyltrimethylsilylmethyl platinum.

10. The compound [1-methyl-3-(2'-naphthyl)cyclopentadienyl]dimethyltrimethylsilylmethyl platinum.

11. The compound [1-methyl-3-(9'-phenanthryl)cyclopentadienyl]dimethyltrimethylsilylmethyl platinum.

12. A method for making platinum (IV) compounds of the formula, $$[(R^1)_a(R^2)_bCp]Pt(R^3R^4)Q$$

where $R^1$ is a $C_{6-20}$ aromatic radical, $R^2$, $R^3$, and $R^4$ are each independently a $C_{1-22}$ aliphatic organic radical, Cp is a cyclopentadienyl radical, Q is a silicon-containing organic sensitizing group, "a" and "b" are whole numbers independently equal to 0 to 5 inclusive, and the sum of "a+b" is equal to 0 to 5 inclusive, comprising, effecting reaction between a cyclopentadienide compound of the formula $$(R^1)_a(R^2)_bCpM,$$

and a platinum (IV) compound of the formula, $$XPt(R^3R^4)Q,$$

where M is a metallic anion, and X is an anionic leaving group.

13. A method in accordance with claim 12, where X is halogen.

14. A method in accordance with claim 12, where $R^1$ is phenanthryl.

15. A method in accordance with claim 12, where $R^1$ is naphthyl.

16. A method in accordance with claim 12, where Q is $-R^5Si(R^6)_3$, $R^6$ is a $C_{1-12}$ organic radical, and $R^5$ is a $C_{1-4}$ alkylene or alkylidene radical.

17. A platinum (IV) compound having the formula, $$XPt(R^3R^4)Q,$$

where Q is a silicon-containing group having the formula, $$-R^5Si(R^6)_3,$$

X is an anionic leaving group, $R^3$ and $R^4$ are each independently a $C_{1-22}$ aliphatic organic radical, $R^6$ is a $C_{1-12}$ organic radical, and $R^5$ is a $C_{1-4}$ alkylene or alkylidene radical.

18. A platinum(IV) compound in accordance with claim 17, where X is a halogen radical.

19. The compound $IPt(CH_3)_2CH_2Si(CH_3)_3$.

20. A method for making a platinum (IV) compound having the formula, $$XPt(R^3R^4)Q,$$

comprising the steps of, (a) effecting a reaction between (i) a platinum (II) compound, $ZPt(R^3)X$, and (ii) a silicon-containing aliphatic sensitizing group, MQ, to form a platinum (II) compound having the formula, $$ZPt(R^3)Q, \text{ and}$$

(b) effecting the displacement of Z by effecting reaction between the platinum (II) compound of (a) and a haloaliphatic compound $XR^4$, where Z is a $C_{7-10}$ cyclodienyl group, Q is $-R^5Si(R^6)_3$, M is a metallic anion, X is an anionic leaving group, $R^3$ and $R^4$ are each independently a $C_{1-22}$ aliphatic organic radical, $R^6$ is a $C_{1-12}$ organic radical, and $R^5$ is a $C_{1-4}$ alkylene or alkylidene radical.

21. A method for making a platinum (IV) compound in accordance with claim 20, where X is a halogen.

22. A method for making a platinum (IV) compound in accordance with claim 20, where Z is a 1,4-cyclooctadienyl group.

23. A method for making a platinum (IV) compound having the formula, $$IPt(CH_3)_2CH_2Si(CH_3)_3,$$

comprising the steps of (c) effecting reaction between a platinum (II) compound, $C_8H_{12}Pt(CH_3)Cl$, and a silicon-containing aliphatic sensitizing group LiCH$_2$Si(CH$_3$)$_3$, to form a platinum (II) compound having the formula, C$_8$H$_{12}$Pt(CH$_3$)CH$_2$Si(CH$_3$)$_3$, and (d) effecting reaction between the platinum (II) compound of (c) and methyl iodide.

24. An irradiation-curable silicone composition comprising, (a) a polydiorganosiloxane having at least two alkenyl radicals attached to silicon by carbon-silicon bonds, where the alkenyl radicals can be in the terminal position, or in the polymer backbone, or a combination thereof, (b) a silicon hydride cross-linker, and, (c) an effective amount of a photo-active cyclopentadienylplatinum (IV) compound having a trisubstituted-silyl aliphatic group attached to platinum by carbon-platinum bonds which is sufficient to effect the cure of the irradiation-curable silicone composition.

25. An irradiation-curable silicone composition comprising, (d) a polydiorganosiloxane having at least two alkenyl radicals attached to silicon by carbon-silicon bonds, where the alkenyl radicals can be in the terminal position, or in the polymer backbone, or a combination thereof, (e) a silicon hydride cross-linker, and, (f) an effective amount of a photo-active platinum (IV) compound having the formula,

[(R$^1$)$_a$(R$^2$)$_b$Cp]Pt(R$^3$R$^4$)Q, which is sufficient to effect the cure of the irradiation-curable silicone composition, where R$^1$ is a C$_{6-20}$ aromatic radical, R$^2$, R$^3$, and R$^4$ are each independently a C$_{1-22}$ aliphatic organic radical, Cp is a cyclopentadienyl radical, Q is a silicon-containing organic sensitizing group, "a" and "b" are whole numbers independently equal to 0 to 5 inclusive, and the sum of "a+b" is equal to 0 to 5 inclusive.

26. An irradiation-curable silicone composition consisting essentially of, (g) a polydiorganosiloxane having at least two alkenyl radicals attached to silicon by carbon-silicon bonds, where the alkenyl radicals can be in the terminal position, or in the polymer backbone, or a combination thereof, (h) a silicon hydride cross-linker, and, (i) a photo-active platinum (IV) compound selected from the group consisting of (cyclopentadienyl)dimethyltrimethylsilylmethylplatinum, [1-methyl-3-(2'-naphthyl)cyclopentadienyl]dimethyltrimethylsilylmethylplatinum, and [1-methyl-3-(9'-phenanthryl)-cyclopentadienyl]dimethyltrimethylsilylmethylplatinum, in an effective amount which is sufficient to effect the cure of the Irradiation-curable silicone composition.

27. A method of coating a substrate with a cured tack-free silicone film, which comprises, (1) applying onto the surface of the substrate to a thickness of about 0.5 to about 5 mil, an irradiation-curable silicone composition comprising, (a) a polydiorganosiloxane having at least two alkenyl radicals attached to silicon by carbon-silicon bonds, where the alkenyl radicals can be in the terminal position, or in the polymer backbone, or a combination thereof, (b) a silicon hydride cross-linker, and, (c) an amount of a photo-active cyclopentadienylplatinum (IV) compound having a trisubstituted-silyl aliphatic group attached to platinum by carbon-platinum bonds which is sufficient to effect the cure of the irradiation-curable silicone composition, and (2) irradiating the surface of the applied irradiation-curable silicone composition with light in the range of 240–400 nm.

28. A method according to claim 27 wherein, the photo-active cyclopentadienylplatinum (IV) compound has the formula

[(R$^1$)$_a$(R$^2$)$_b$Cp]Pt(R$^3$R$^4$)Q, where R$^1$ is a C$_{6-20}$ aromatic organic radical, R$^2$, R$^3$, and R$^4$ are each independently a C$_{1-22}$ aliphatic organic radical, Cp is a cyclopentadienyl radical, Q is a silicon-containing organic sensitizing group of the formula —R$^5$Si(R$^6$)$_3$, R$^6$ is a C$_{1-12}$ organic radical, and R$^5$ is a C$_{1-4}$ alkylene or alkylidene radical, "a" and "b" are whole numbers independently equal to 0 to 5 inclusive, and the sum of "a+b" is equal to 0 to 5 inclusive.

29. A method according to claim 27, where the photo-active cyclopentadienylplatinum (IV) compound is [1-methyl-3-(9'-phenanthryl)cyclopentadienyl]trimethyl platinum.

30. A method according to claim 27, where the substrate is cellulose-based.

31. A substrate coated with an irradiation-curable silicone composition comprising, a platinum (IV) compound having the formula,

[(R$^1$)$_a$(R$^2$)$_b$Cp]Pt(R$^3$R$^4$)Q, and any reaction products thereof, where R$^1$ is a C$_{7-20}$ aromatic organic radical, R$^2$, R$^3$, and R$^4$ are each independently a C$_{1-22}$ aliphatic organic radical, Cp is a cyclopentadienyl radical, "a" and "b" are whole numbers independently equal to 0 to 5 inclusive, and the sum of "a+b" is equal to 0 to 5 inclusive.

32. A substrate according to claim 31, in which the silicone coating composition has been irradiation-cured.

33. A substrate according to claim 31, which is cellulose-based.

34. A substrate according to claim 33, in which the silicone coating composition has been irradiation-cured.

* * * * *